United States Patent
Balasubramhanya et al.

(10) Patent No.: US 6,368,975 B1
(45) Date of Patent: Apr. 9, 2002

(54) METHOD AND APPARATUS FOR MONITORING A PROCESS BY EMPLOYING PRINCIPAL COMPONENT ANALYSIS

(75) Inventors: Lalitha Balasubramhanya, Santa Clara; Moshe Sarfaty, Cupertino; Jed Davidow; Dimitris Lymberopoulos, both of Santa Clara, all of CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/348,972

(22) Filed: Jul. 7, 1999

(51) Int. Cl.$^7$ ............................................. H01L 21/302
(52) U.S. Cl. ..................... 438/706; 438/707; 438/710
(58) Field of Search ..................... 438/5, 6, 7, 8, 438/9, 10, 11, 12, 13, 690, 706, 712, 710; 216/58, 59, 60

(56) References Cited

U.S. PATENT DOCUMENTS

| | | | | |
|---|---|---|---|---|
| 4,312,732 A | * | 1/1982 | Degenkolb et al. | 204/192.33 |
| 5,653,894 A | * | 8/1997 | Ibbotson et al. | 216/59 |
| 5,711,843 A | * | 1/1998 | Jahns | 216/58 |
| 5,885,472 A | * | 3/1999 | Miyazaki et al. | 216/60 |
| 5,966,586 A | * | 10/1999 | Hao | 438/7 |
| 6,017,414 A | | 1/2000 | Koemtzopoulos et al. | |

OTHER PUBLICATIONS

Shadmehr et al., J. Electrochem. Soc., vol. 139, No. 3, pp. 907–914, Mar. 1992.*

The EP2000 Plasma Diagnostic System Datasheet, CETAC Corporation, pp. 2–5.

Han Chen and D.S. Boning, "Data–Rich Multivariate Time–Series Detection/Diagnosis Using Extensions to Principal Components Analysis", SIMA/LFM Workshop on Industrial Diagnostics (15pp) (May 6, 1998).

Technical Presentation, "Eigensystem Trend Analysis (ETA)," Verity Instruments, Inc. (5pp) (Feb. 24, 1999).

* cited by examiner

*Primary Examiner*—Benjamin L. Utech
*Assistant Examiner*—Duy-Vu Deo
(74) *Attorney, Agent, or Firm*—Dugan and Dugan; Joseph Bach

(57) ABSTRACT

A method and apparatus for monitoring a process by employing principal component analysis are provided. Correlated attributes are measured for the process to be monitored (the production process). Principal component analysis then is performed on the measured correlated attributes so as to generate at least one production principal component; and the at least one production principal component is compared to a principal component associated with a calibration process (a calibration principal component). The calibration principal component is obtained by measuring correlated attributes of a calibration process, and by performing principal component analysis on the measured correlated attributes so as to generate at least one principal component. A principal component having a feature indicative of at least one of a desired process state, process event and chamber state then is identified and is designated as the calibration principal component. Preferably the at least one production principal component is compared to the calibration principal component by computing the inner product of the calibration and production principal components.

14 Claims, 15 Drawing Sheets

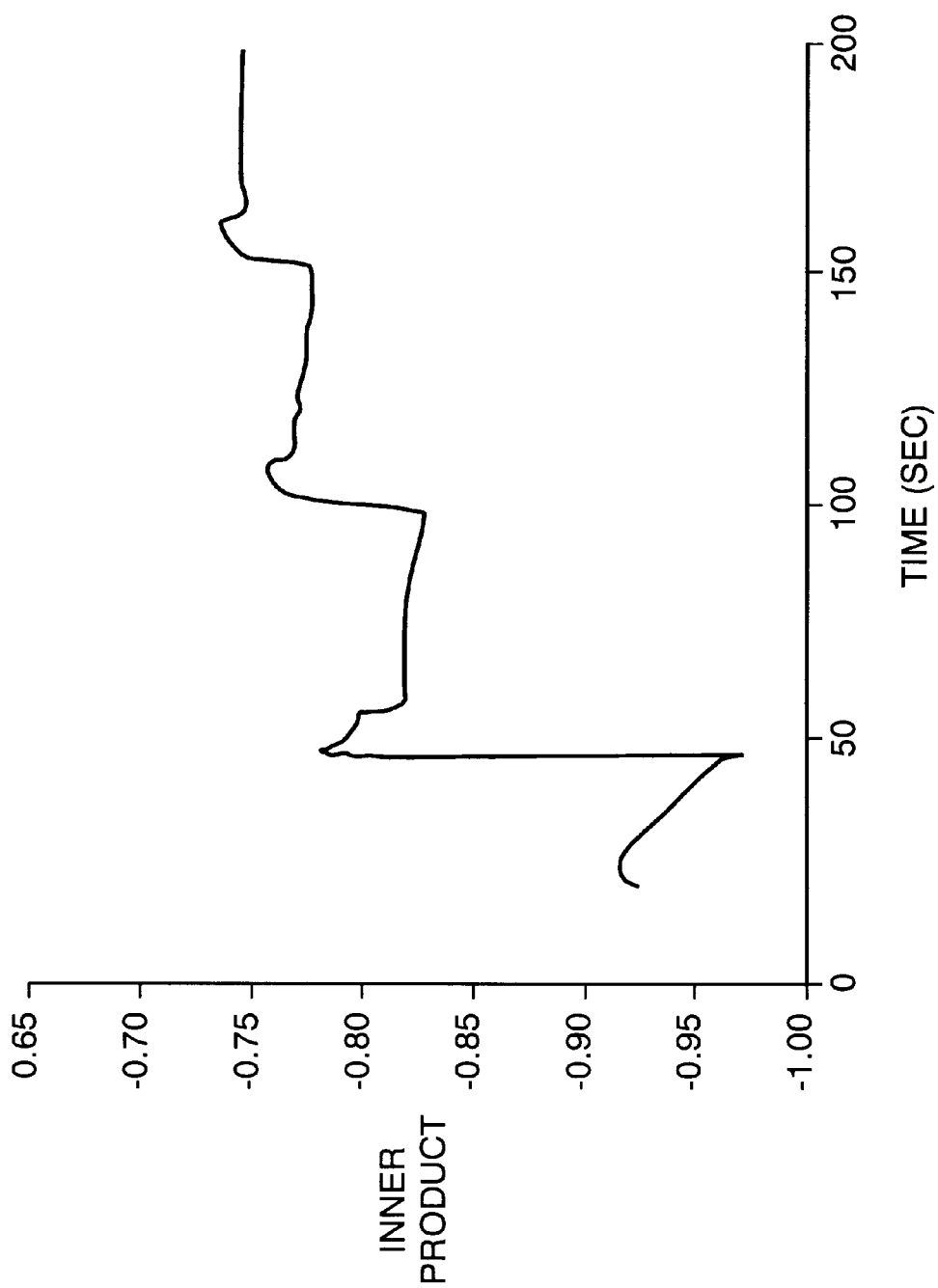

METHOD AND APPARATUS FOR MONITORING A PROCESS BY EMPLOYING PRINCIPAL COMPONENT ANALYSIS

FIELD OF THE INVENTION

The present invention relates to techniques for monitoring a process, and more particularly to a method and apparatus for monitoring a process by employing principal component analysis.

BACKGROUND OF THE INVENTION

Within the semiconductor industry, an ever present need exists for improved process repeatability and control. For example, during the formation of a typical metal-layer-to-metal-layer interconnect, a dielectric layer is deposited over a first metal layer, a via hole is etched in the dielectric layer to expose the first metal layer, the via hole is filled with a metal plug and a second metal layer is deposited over the metal plug (e.g., forming an interconnect between the first and the second metal layers). To ensure the interconnect has low contact resistance, all dielectric material within the via hole must be etched from the top surface of the first metal layer prior to formation of the metal plug thereon; otherwise, residual high-resistivity dielectric material within the via hole significantly degrades the contact resistance of the interconnect. Similar process control is required during the etching of metal layers (e.g., Al, Cu, Pt, etc.), polysilicon layers and the like.

Conventional monitoring techniques provide only a rough estimate of when a material layer has been completely etched (i.e., endpoint). Accordingly, to accommodate varying thicknesses of material layers (e.g., device variations) or varying etch rates of material layers (e.g., process/process chamber variations), an etch process may be continued for a time greater than a predicted time for etching the material layer (i.e., for an over-etch time). Etching for an over-etch time ensures that all material to be removed is removed despite device variations and process/chamber variations that can vary etch time.

While over-etch times ensure complete etching, over-etching increases the time required to process each semiconductor wafer and thus decreases wafer throughput. Further, the drive for higher performance integrated circuits requires each generation of semiconductor devices to have finer dimensional tolerances, rendering over-etching increasingly undesirable. The smaller open areas required for reduced dimension device structures also reduce the intensity of commonly monitored electromagnetic emissions (e.g., reaction product emissions) so as to render monitoring techniques employing narrow band intensity measurements increasingly difficult and inaccurate. Accordingly, a need exists for improved techniques for monitoring semiconductor manufacturing processes such as etch processes, chamber cleaning processes, deposition processes and the like.

SUMMARY OF THE INVENTION

The present inventors have discovered that by measuring correlated attributes of a process (e.g., a plurality of electromagnetic emissions, and/or process temperature, process pressure, RF power, etc.), and by employing principal component analysis to analyze the correlated attributes, process state, process event and, if applicable, chamber state information may be easily and accurately obtained for the process. Exemplary process state information that may be obtained includes RF power, plasma reaction chemistry, etc.; exemplary process event information that may be obtained includes whether a particular material has been etched through or away (i.e., breakthrough), whether a desired process is complete (e.g., etching or deposition), when a wafer is improperly held (i.e., improper "chucking"), etc.; and, if applicable, exemplary chamber state information that may be obtained includes whether a chamber contains a fault, whether a chamber's operation is similar to its previous operation or to another chamber's operation (i.e., chamber matching), etc.

In accordance with the invention, correlated attributes are measured for the process to be monitored (i.e., the production process), and principal component analysis is performed on the measured correlated attributes so as to generate at least one production principal component. The at least one production principal component then is compared to a principal component associated with a calibration process (i.e., a calibration principal component).

The calibration principal component is obtained by measuring correlated attributes of a calibration process (e.g., preferably the same process as the production process, but typically for non-production purposes), and by performing principal component analysis on the measured correlated attributes so as to generate at least one principal component. A principal component having a feature indicative of at least one of a desired process state, process event and chamber state then is identified and is designated as the calibration principal component. Preferably the at least one production principal component is compared to the calibration principal component by computing the inner product of the calibration and production principal components. The calibration and production principal components also may be compared by employing other techniques such as the "coherence" function found in the mathematics software package MAT-LAB™ marketed by Mathworks, Inc. or by computing the scalar magnitude or "norm" of the difference between the calibration and production principal components.

By thus comparing calibration and production principal components, process event, process state and chamber state information may be obtained rapidly (e.g., in real time) and with a high degree of accuracy. Processes thereby may be monitored and processing parameters/conditions adjusted in real time, over-processing times such as over-etch times avoided and process yield and throughput significantly increased.

BRIEF DESCRIPTION OF THE DRAWINGS

The present invention is described with reference to the accompanying drawings. In the drawings, like reference numbers indicate identical or functionally similar elements. Additionally, the left-most digit of a reference number identifies the drawing in which the reference number first appears.

FIG. 8 is a graph of the inner product of calibration and production first principal components generated under processing conditions that mimic process drift;

DETAILED DESCRIPTION

As stated, the present inventors have discovered that by measuring correlated attributes of a process, and by employing principal component analysis to analyze the correlated attributes, process state, process event and, if applicable, chamber state information may be easily and accurately obtained for the process. For convenience, the present invention is described herein primarily with reference to plasma etch processes and plasma-based correlated attributes (e.g., plasma electromagnetic emissions, RF power, chamber pressure, throttle valve position, etc.). However, the invention may be similarly employed to monitor any other process whether or not a plasma is employed and whether or not related to semiconductor device processing such as deposition processes, cleaning processes, chemical-mechanical polishing processes, etc. Monitorable correlated attributes for these types of processes include but are not limited to temperature, pressure, weight gain/loss, plasma emissions, RF power, throttle valve position, etc.

Figure 1A:
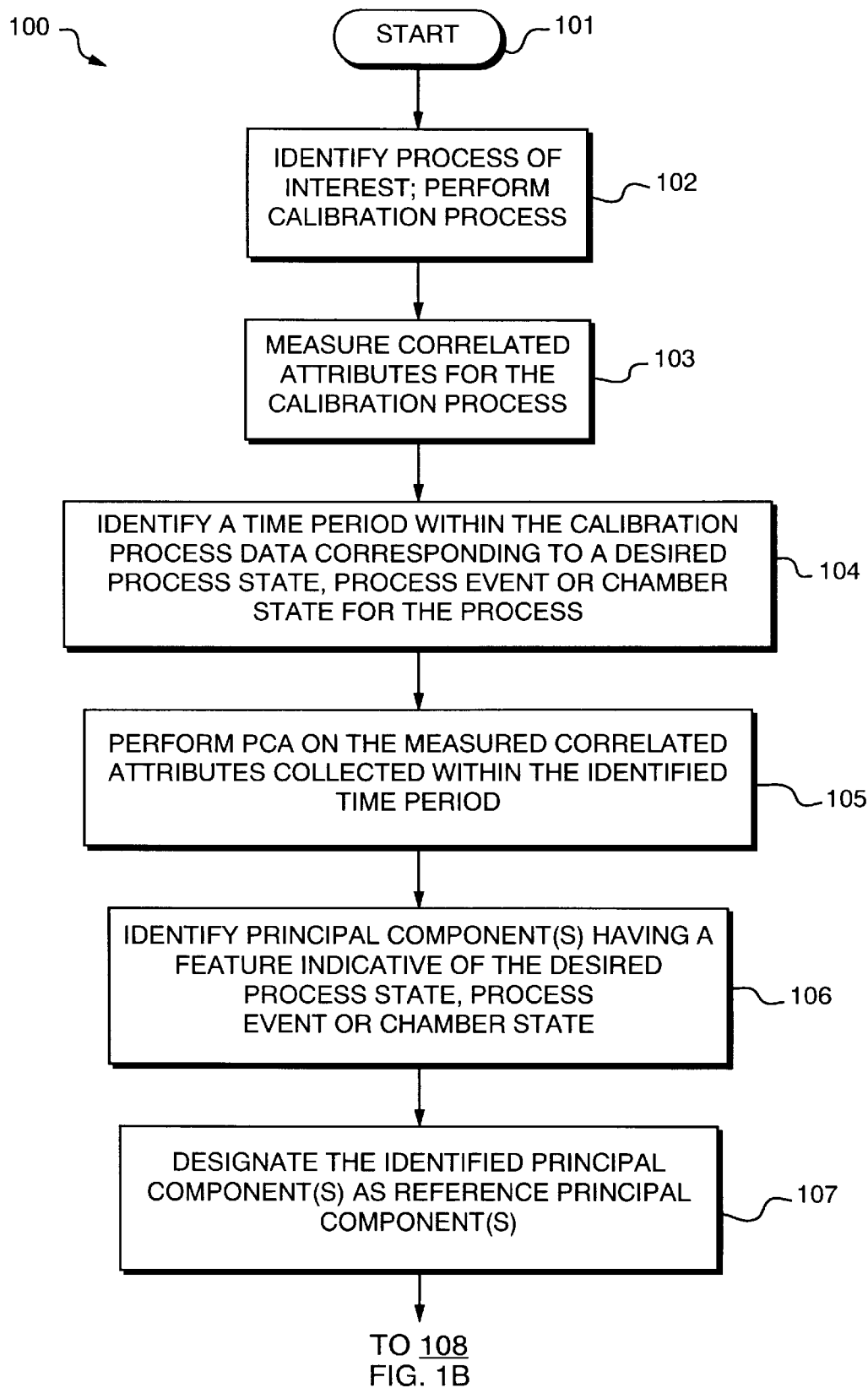
FIGS. 1A and 1B are a flowchart of an inventive monitoring technique for monitoring a generic process in accordance with the present invention.
Figure 1B:
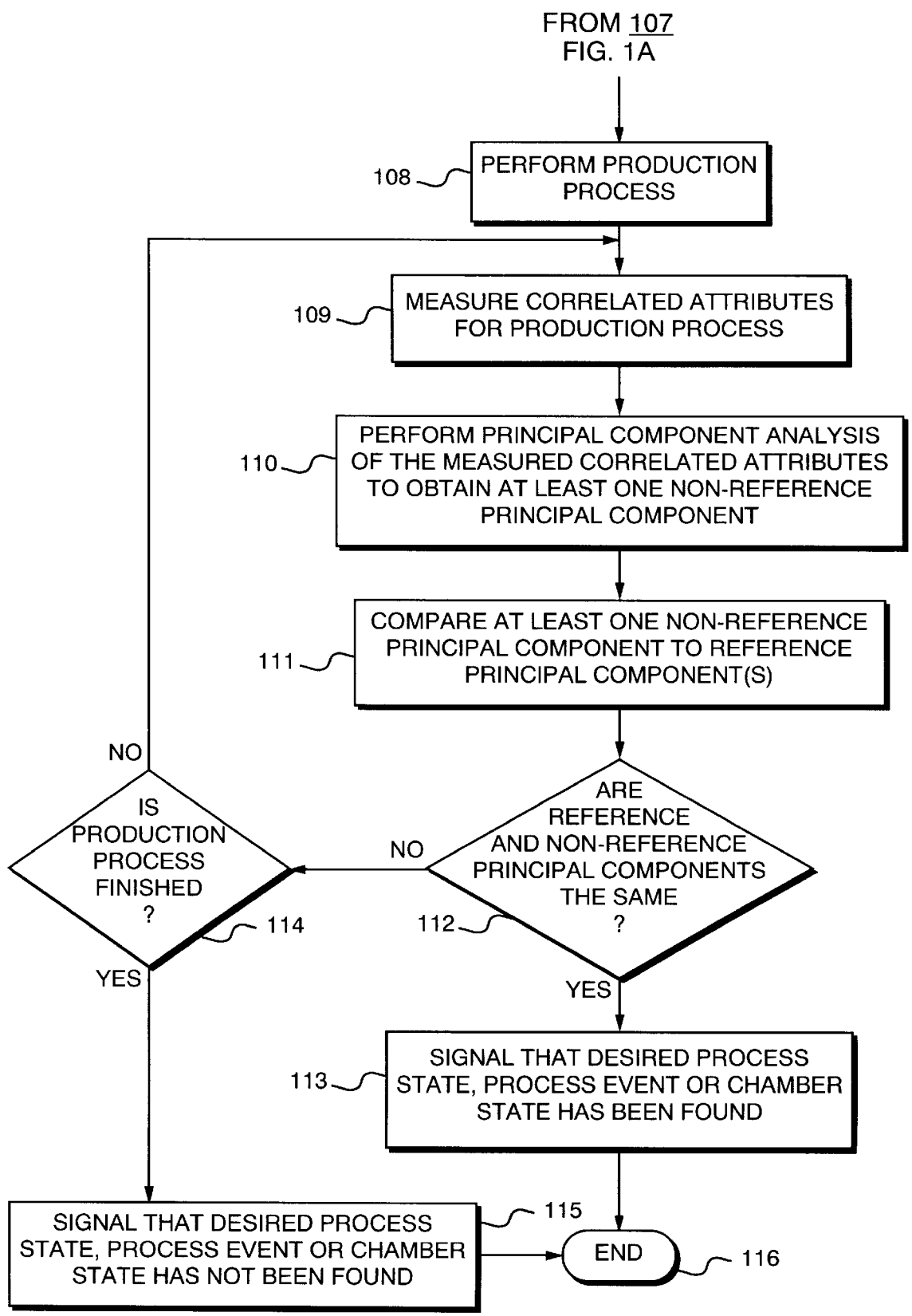

FIGS. 1A and 1B are a flowchart of an inventive monitoring technique 100 for monitoring a generic process in accordance with the present invention. The inventive monitoring technique 100 starts in Step 101.

In Step 102, a process to be monitored (i.e., a production process) is identified and a calibration process is performed. In most cases, the calibration process and the production process employ the same process parameters (e.g., identical flow rates, substrate temperatures, chamber pressures, etc.). However, as described below with reference to FIG. 8, to determine the sensitivity of the inventive monitoring technique to process drift or to other process variations within the production process, it may be desirable to vary one or more process parameters of the calibration process such as process gas flow rates, process temperature and the like relative to the production process.

During performance of the calibration process, in Step 103, sets of correlated attributes of the calibration process are measured (preferably at a periodic rate) such as a plurality of plasma emission wavelengths for a plasma process, and/or process temperature, throttle valve position, process pressure, or any other correlated attributes. As is known, multiple correlated attributes are required to provide sufficient information for principal component analysis.

In Step 104, a time or time period is identified within the collected calibration process data that corresponds to a desired process state, process event or chamber state for the calibration process. This time or time period identification typically is performed following the calibration process and may therefore be conducted using sophisticated, albeit time consuming, identification techniques not suitable for real-time use during a process (e.g., during a production process such as an oxide etch for a contact opening of a semiconductor device). For example, if the calibration process is an etch process, the endpoint or breakthrough time for etching a material layer may be determined by performing a series of different duration etches under identical process conditions and by examining the cross section (e.g., via scanning electron or transmission electron microscopy techniques) of the material layer for each etch duration to determine the precise endpoint or breakthrough time for the etching of the material layer. Similarly, process gas flow rates, chamber pressure, process temperature, etc., may be measured employing sophisticated measurement techniques to characterize chamber process state over time or for chamber matching purposes.

In Step 105, principal component analysis (PCA) is performed on the measured correlated attributes for the calibration process collected near the identified process state, process event or chamber state time. For example, a window of data (e.g., a window comprising data for ten different measurement times, or any other window size) comprising correlated attribute data taken at times before, during and/or after the event can be examined. The correlated attribute data within the window is used to form a matrix having rows comprising the measured correlated attribute data and columns comprising the time each attribute set was measured. The data within the matrix may be analyzed as collected but preferably is mean centered or is mean centered and scaled (as described below). Thereafter a singular value decomposition is performed on the matrix and principal component eigenvectors are generated for the measured correlated attribute data within the matrix. Typically, two to three principal components are sufficient to capture 80% of the changes that occur within the measured correlated attribute data within the matrix.

In Step 106, the generated principal components for the measured correlated attributes of the calibration process are examined for features indicative of the desired process state, process event or chamber state of the calibration process. As described below, typically one principal component will contain a sharp feature indicative of the desired process state, process event or chamber state. In Step 107 the identified principal component is designated as a "calibration" principal component for the desired process event, process state or chamber state. Once obtained, the calibration principal component may be used to rapidly identify the desired process event, process state or chamber state during the performance of a production process (e.g., in real time), or thereafter, without requiring the complicated and/or time consuming experiments and analysis employed to identify the time within the calibration process corresponding to the desired process event, process state or chamber state (described below).

In Step 108, the production process is performed (e.g., typically with the same process parameters as the calibration process), and, in Step 109, correlated attributes for the production process are measured. Preferably during the production process, each time correlated attributes are measured, the attributes are stored within an evolving window wherein new measured correlated attributes are added to the window and old measured correlated attributes are dropped from the window over time until all measured correlated attributes pass through the window. The evolving window for production process attributes may be the same size as or a different size from the window used to compute calibration principal components.

In Step 110, each time new measured correlated attributes are added to the evolving window, principal component analysis is performed on the measured correlated attribute data therein to generate one or more principal components for the production process (e.g., one or more production principal components). Alternatively, principal component analysis may be performed only near the expected time for the desired process state, process event, or chamber state.

In Step 111, at least one production principal component (e.g., the same order principal component as the calibration principal component), is compared to the calibration principal component. The production and calibration principal components may be compared by any method (e.g., subtraction, subtraction followed by a norm operation, division, with a coherence-type function, etc.) but preferably are compared by computing the dot or inner product of the two principal components. Because the two principal components have unit length, the inner product of the calibration and production principal components is approximately +1.0 if the calibration and production principal components have approximately the same features that change in the same directions, is approximately −1.0 if the calibration and production principal components have approximately the same features that change in opposite directions and is approximately zero if the calibration and production principal components do not match. Thus, by taking the inner product of the calibration and production principal components, the production principal component can be easily compared to the calibration principal component.

In Step 112, a determination is made as to whether the calibration and production principal components are approximately the same. If so, in Step 113 a signal is generated indicating that the desired process state, process event or chamber state has been found during the production process, and in Step 116, the inventive monitoring technique 100 ends. As described further below, the signal generated indicating that the desired process state, process event or chamber state has been found may comprise, for example, an indicator that endpoint or breakthrough has been reached, that process drift has been detected, that a chamber fault has been detected, that chamber matching has been established, etc.

If in Step 112 the calibration and production principal components are determined not to match, in Step 114, a determination is made as to whether the production process has ended or has proceeded further than expected without detection of the desired process state, process event or chamber state. If so, in Step 115 a signal (e.g., a warning signal) is generated indicating that the desired process state, process event or chamber state was not found during the production process. Control then passes to Step 116 wherein the inventive monitoring technique 100 ends.

If in Step 114 the production process has not ended or has not proceeded further than expected, control passes to Step 109 where additional correlated attributes are measured for the production process and the additional measured correlated attributes are added to the evolving window. Principal component analysis then is performed on the data within the evolving window (Step 110), a new production principal component is compared to the calibration principal component (Step 111) as previously described. This process repeats until either the desired process state, process event or chamber state is found, or until the production process ends or proceeds further than expected. The inventive monitoring technique 100 now is described with reference to a plasma process.

Figure 2:
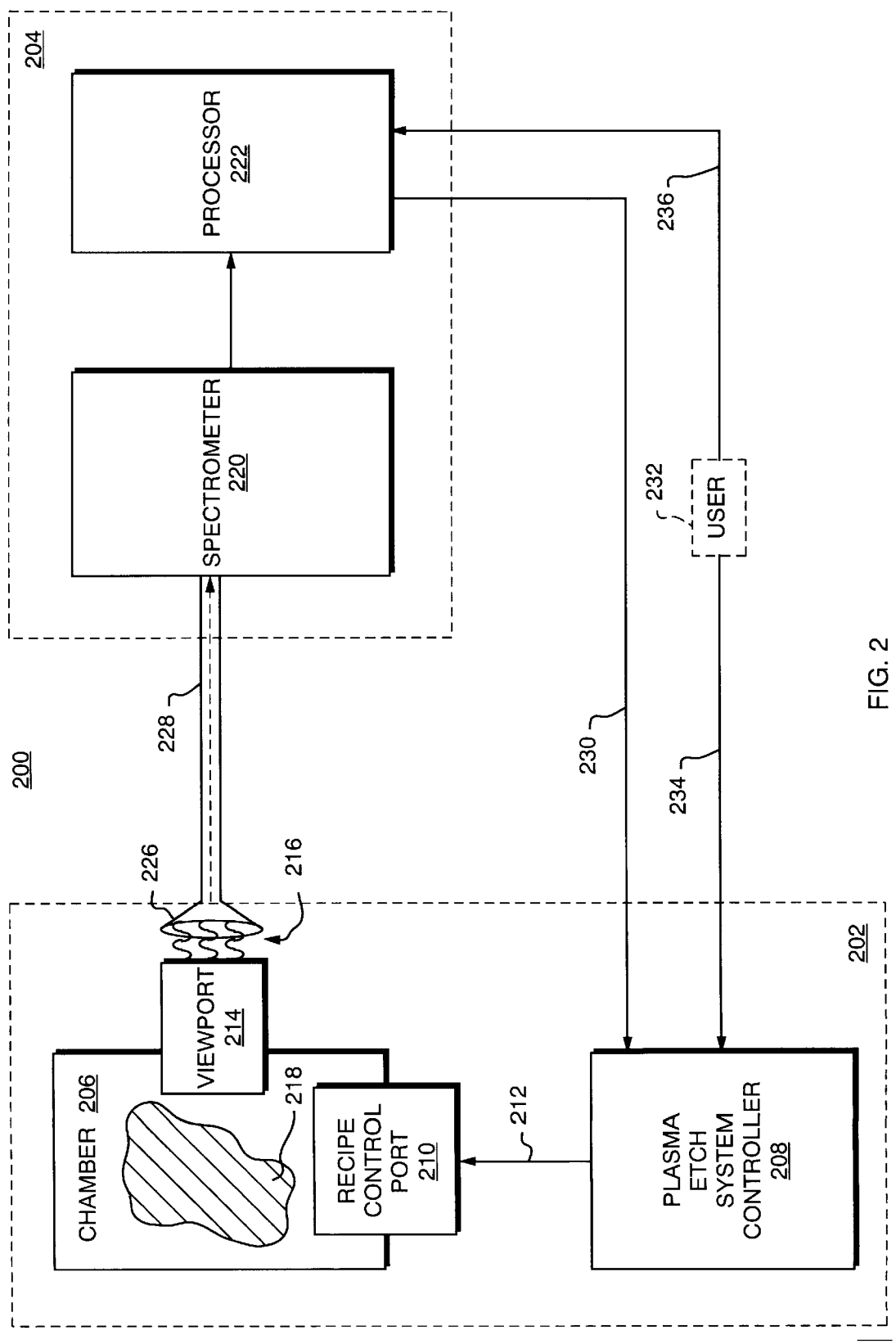
FIG. 2 is a schematic diagram of an inventive processing system comprising a plasma etching system and an inventive process monitoring system coupled thereto in accordance with the present invention.

FIG. 2 is a schematic diagram of a processing system 200 comprising a conventional plasma etching system 202 and an inventive process monitoring system 204 coupled thereto in accordance with the present invention. As used herein, "coupled" means coupled directly or indirectly so as to operate.

The conventional plasma etching system 202 comprises a plasma chamber 206 coupled to a plasma etch system controller 208 via a recipe control port 210 and via a first control bus 212. It will be understood that while a single interface (e.g., the recipe control port 210) is shown between the plasma chamber 206 and the plasma etch system controller 208 for convenience, in general, the plasma etch system controller 208 may interface the various mass flow controllers, RF generators, temperature controllers, etc., associated with the plasma chamber 206 via a plurality of interfaces (not shown).

The plasma chamber 206 comprises a viewport 214 for outputting electromagnetic emissions (e.g., primarily optical wavelengths within the range from about 180 to 1100 nanometers, generally represented as 216 in FIG. 2) from a plasma 218 sustained within the plasma chamber 206 (described below). The plasma electromagnetic emissions 216 comprise emissions from a large number of plasma species (e.g., process gasses, reaction products, etc.) and represent one type of correlated attributes that may be measured for a plasma process. Note that the viewport 214 is shown positioned on the side of the plasma chamber 206, but may be positioned at any other location (e.g., on the top or bottom of the chamber 206) if desired.

The inventive process monitoring system 204 comprises a spectrometer 220 coupled to a processing mechanism (e.g., a processor 222). The spectrometer 220 is positioned to collect the electromagnetic emissions 216 from the plasma 218 and to provide intensity information regarding a plurality of plasma electromagnetic emission wavelengths to the processor 222. The spectrometer 220 preferably comprises an Ocean Optics Model No. S2000 Spectrometer employing a 2048 channel CCD array for providing intensity information to the processor 222 regarding 2048 plasma electromagnetic emission wavelengths spanning a wavelength range of about 180 to 850 nanometers. It will be understood that other spectrometers may be employed and other wavelength ranges may be monitored. A lens 226 and/or a fiber optic cable 228 preferably are disposed between the viewport 214 and the spectrometer 220 for improving collection of the electromagnetic emissions 216 by the spectrometer 220 (e.g., by coupling the electromagnetic emissions 216 into the fiber optic cable 228 via the lens 226 and by transporting the electromagnetic emissions 216 to the spectrometer 220 via the fiber optic cable 228). Other alternative configurations for collecting electromagnetic emissions from the plasma 218 may be employed in place of the spectrometer 220 such as a photodiode array wherein each photodiode monitors a different wavelength or a different wavelength spectrum. If desired, a bundle of fiber optic cables may be coupled to the diode array wherein each fiber optic cable within the bundle is coupled to a unique photodiode and supplies electromagnetic emissions thereto. Similarly, diffraction gratings, prisms, optical filters (e.g., glass filters) and other wavelength selective devices may be employed with a plurality of detectors (e.g., photodiodes, photomultipliers, etc.) to provide information regarding a plurality of electromagnetic emission wavelengths to the processor 222. The processor 222 is coupled to the plasma etch system controller 208 via a second control bus 230.

In operation, a user 232 (e.g., a person in charge of a wafer fabrication process) supplies (via a third control bus 234) the plasma etch system controller 208 with a set of instructions for generating the plasma 218 within the plasma chamber 206 (i.e., a plasma recipe). Alternatively, a remote computer system for running a fabrication process that includes the processing system 200, a manufacturing execution system or any other fabrication control system may supply the plasma etch system controller 208 with a plasma recipe (e.g., as supplied by the user 232 or as stored within a plasma recipe database). A typical plasma recipe includes processing parameters such as the pressure, temperature, power, gas types, gas flow rates and the like used to initiate and maintain the plasma 218 within the plasma chamber 206 during plasma processing. For example, to perform aluminum etching within the plasma chamber 206, a typical plasma recipe would include at least the following: a desired chamber pressure, a desired process temperature, a desired RF power level, a desired wafer bias, desired process gas flow rates (e.g., desired flow rates for process gasses such as Ar, $BCl_3$ or $Cl_2$), etc. Once the plasma etch system controller 208 receives a plasma recipe from the user 232, from a remote computer system, from a manufacturing execution system, etc., the plasma recipe is supplied to the recipe control port 210 via the first control bus 212, and the recipe control port 210 (or the plasma etch system controller 208 itself if the recipe control port 210 is not present) establishes and maintains within the plasma chamber 206 the processing parameters specified by the plasma recipe.

During a plasma process within the plasma chamber 206, the plasma 218 generates electromagnetic emissions having wavelengths primarily in the optical spectrum (e.g., from about 180 to 1100 nanometers), although both ultra-violet and infrared wavelengths also may result. A portion of these electromagnetic emissions (e.g., the electromagnetic emissions 216) travel through the viewport 214 and reach the inventive process monitoring system 204. Note that while the electromagnetic emissions 216 are represented generally by three emission wavelengths in FIG. 2, it will be understood that the electromagnetic emissions 216 typically comprise many more wavelengths.

With reference to FIG. 2, the spectrometer 220 receives the electromagnetic emissions 216 via the lens 226 and the fiber optic cable 228. In response thereto, the spectrometer 220 spatially separates the electromagnetic emissions 216 based on wavelength (e.g., via a prism or a diffraction grating (not shown)), and generates detection signals (e.g., detection currents) for a plurality of the spatially separated wavelengths. In the preferred embodiment, an Ocean Optics Model No. S2000 spectrometer is employed for the spectrometer 220 wherein a 600 lines/millimeter grating blazed at 400 nanometers spatially separates plasma emission wavelengths onto a 2048 linear silicon charge-coupled device array so as to generate 2048 detection currents or 2048 "channels" of detection signal information (i.e., optical emission spectroscopy (OES) information) for plasma emission wavelengths from about 180–850 nanometers. Other wavelength ranges and channel sizes may be employed if desired, and multiple wavelength regions of the plasma spectrum may be examined so as to generate multiple calibration and production principal components which may be compared in accordance with the inventive monitoring technique 100.

Once generated, the OES information is digitized (e.g., via an analog-to-digital converter) and is output to the processor 222 for subsequent processing (described below). The OES information may be output to the processor 222 in analog form if desired. Typically, new 2048 channel OES information (e.g., new correlated attribute data) is collected and supplied to the processor 222 in one second intervals, although other time intervals may be employed.

Because the plasma emission wavelengths collected by the spectrometer 220 comprise emissions from a large number of plasma species, the collected emission wavelengths represent correlated attributes of the plasma process that may be analyzed via principal component analysis. Other suitable correlated attributes of the plasma process include RF power, wafer temperature, chamber pressure, throttle valve position, process gas flow rates and the like. Thus, in accordance with the present invention, correlated attributes (e.g., electromagnetic emissions) of the plasma process are measured via the spectrometer 220, and are supplied to the processor 222 in the form of 2048 channels of OES data. The particular type of processing to be performed by the processor 222 preferably is selected by the user 232 (or by a remote computer system, by a manufacturing execution system, etc.) via a fourth control bus 236.

Figure 3A:
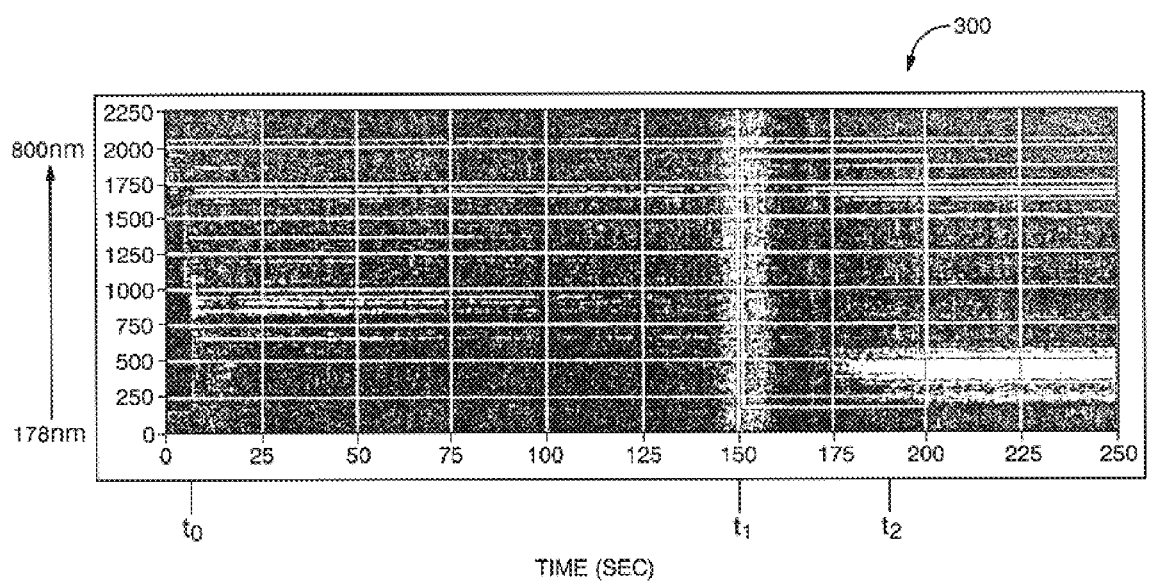
FIG. 3A is a contour graph of mean-centered optical emission spectroscopy (OES) information generated the plasma etching of a silicon dioxide layer within the processing system of FIG. 2.
Figure 3B:
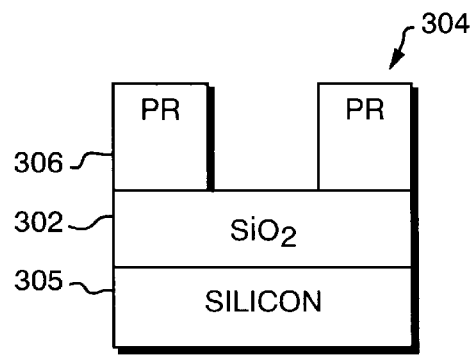
FIG. 3B is a cross-sectional diagram of a multilayer semiconductor structure comprising the silicon dioxide layer etched to obtain the OES information of FIG. 3A.

FIG. 3A is a contour graph of OES data 300 generated during the plasma etching of a silicon dioxide layer 302 of a multilayer semiconductor structure 304 (FIG. 3B). Darker shading in FIG. 3A indicates larger magnitude; and the OES data 300 is mean centered by computing the average wavelength intensity between times $t_1$ and $t_2$ and by subtracting the average wavelength intensity from each measured wavelength intensity. In general, a wavelength intensity occurring at any time t of interest may be mean centered, for example, by computing the average wavelength intensity between times t–10 and t+10 and by subtracting the average wavelength intensity from the measured wavelength intensity.

With reference to FIG. 3B, the multilayer semiconductor structure 304 comprises the silicon dioxide layer 302 deposited on a silicon wafer 305 and having a thickness of about 2000 angstroms, and a photo-resist layer 306 deposited on the silicon dioxide layer 302 and having a thickness of about 8000 angstroms. The photo-resist layer 306 is patterned to expose about 10% of the silicon dioxide layer 302 during etching.

To obtain the OES data 300, the multilayer semiconductor structure 304 is placed within the plasma chamber 206 (e.g., a MxP™ chamber with no magnetic field applied) and the plasma 218 is struck, for example, employing Ar, $CHF_3$ and $CF_4$ as is well known in the art. Electromagnetic emissions having wavelengths from about 180 to 850 nanometers that pass through the viewport 214 are collected by the spectrometer 220 and the non-mean centered OES data 300 is generated by the spectrometer 220. In the preferred embodiment, the OES data 300 is generated by taking a "snap-shot" of the wavelengths output by the plasma 218 every second (e.g., 2048 channels of new wavelength data every second) and by digitizing the data at a rate of about one MHz. Other snap-shot/digitization rates may be employed. As the OES data 300 is collected, each wavelength snap-shot preferably is passed to the processor 222 in real-time to allow for real time process control of the plasma chamber 206 (described below). The processor 222 mean centers the OES data 300.

Figure 3C:
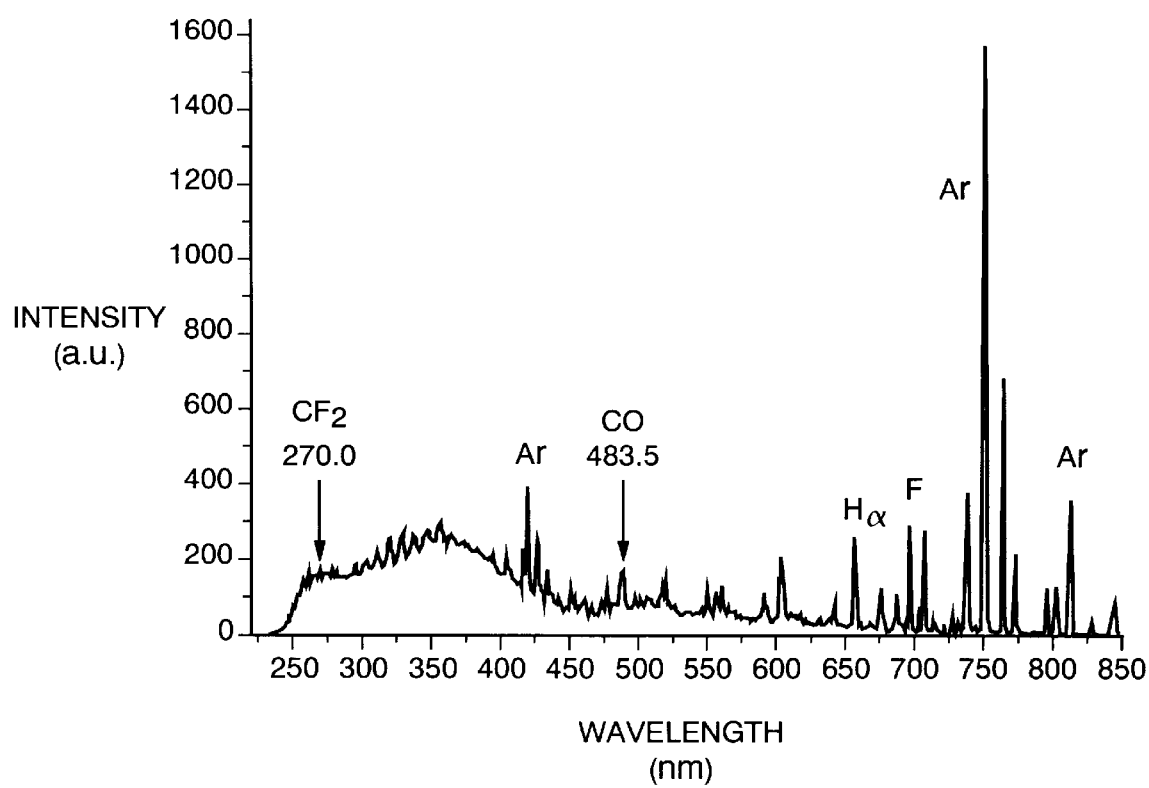
FIG. 3C is a snap-shot of the wavelengths output by a plasma during etching of the silicon dioxide layer of FIG. 3B.

FIG. 3C is a snap-shot of the wavelengths output by the plasma 218 during etching of the oxide layer 302 (about 60 seconds into the etching process). Conventional monitoring techniques such as endpoint detection monitor the change in intensity of individual plasma emissions wavelengths (e.g., the intensity of $CF_2$ or CO lines) over time. However, as feature sizes continue to shrink for each new semiconductor device generation, less material needs to be etched, fewer reaction products are generated during etching, less reactive gasses are consumed during etching, and the changes in individual wavelength intensities that occur during etching become smaller and more difficult to detect within the overall plasma emission spectrum. Because principal component analysis examines multiple correlated attributes (e.g., wavelengths), it is much less sensitive to a decrease in signal intensity of individual emission lines that accompanies a decrease in feature size.

With reference to FIG. 3A, etching of the oxide layer 302 begins at time to and ends somewhere between time $t_1$ and $t_2$. As shown in FIG. 3A, the maximum changes in wavelength intensity for the OES data 300 occur between time $t_1$ and $t_2$, indicative of the etching endpoint for the oxide layer 302. Specifically, near endpoint, a few wavelengths increase in intensity and a few wavelengths decrease in intensity. However, a sharp transition that identifies the exact location of endpoint is not observable.

In accordance with the present invention (and the inventive monitoring technique 100 of FIGS. 1A and 1B), the plasma process used to generate the OES data 300 of FIG. 3A is treated as a calibration process; and the presence and location of the endpoint between times $t_1$ and $t_2$ is verified/obtained by independent means (e.g., by a conventional endpoint technique, by etch studies combined with scanning electron or transmission electron microscopy, etc.). Principal component analysis then is performed (as previously described) on a window of OES data near the predicted endpoint time (e.g., on a window of about twenty wavelength snap-shots encompassing the predicted endpoint time).

Figure 3D:
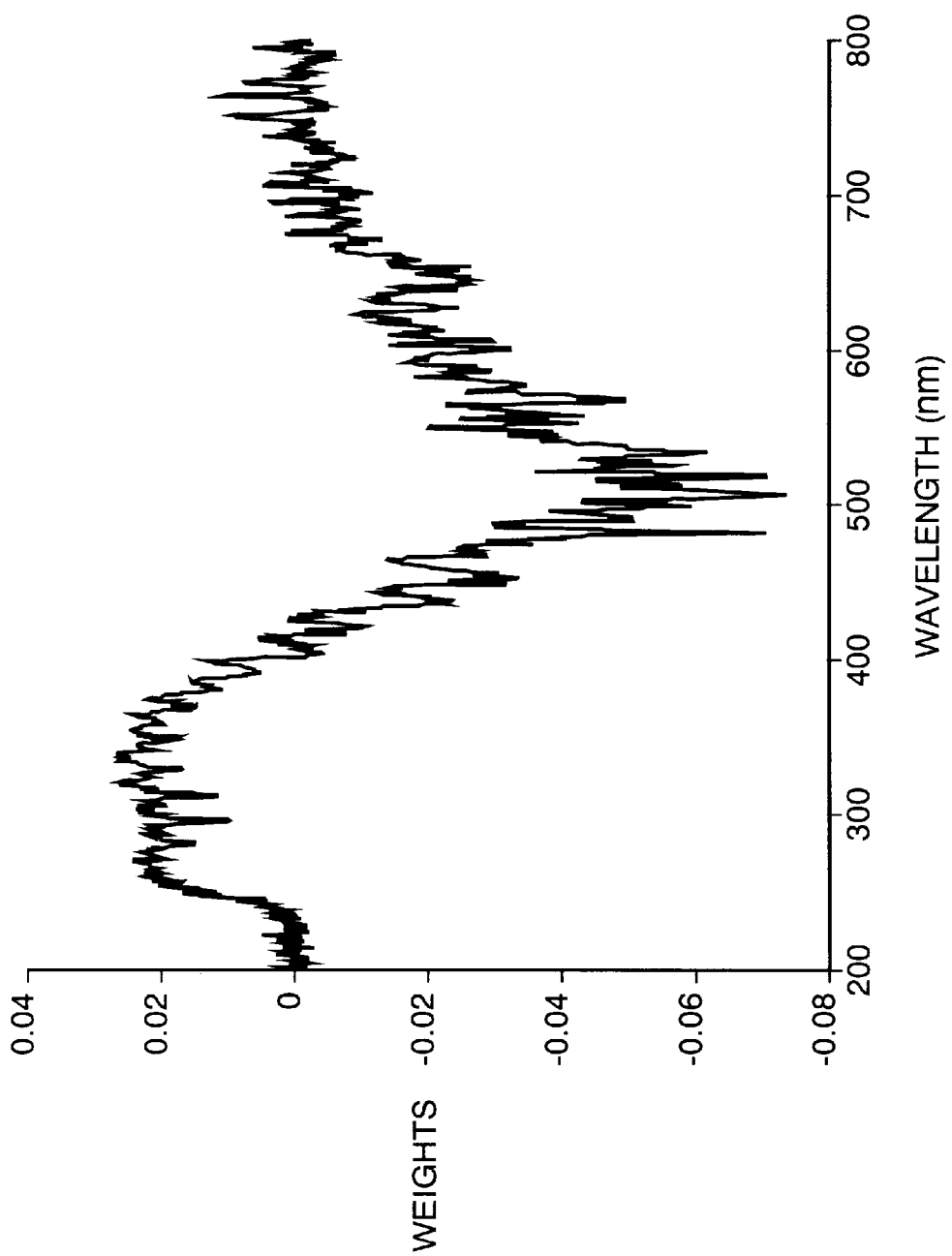
FIG. 3D is a graph of a first principal component generated during etching of the silicon dioxide layer of FIG. 3B.

FIG. 3D is a graph of the first principal component (PC1) for the calibration process used to generate FIGS. 3A–3C, computed in the vicinity of the oxide etching endpoint that falls between times $t_1$ and $t_2$ (FIG. 3A). The PC1 is defined by "weights" associated with each wavelength; and the sign and magnitude of each weight associated with a wavelength indicates the direction and the magnitude of the change associated with the wavelength near endpoint. During subsequent processing under identical conditions, the same PC1 component will be observable near endpoint.

Accordingly, the PC1 of FIG. 3D may serve as a calibration principal component during subsequent "production" processes that "fingerprints" the endpoint event (e.g., the endpoint for the etching of the silicon dioxide layer 302 of FIG. 3B).

Figure 4A:
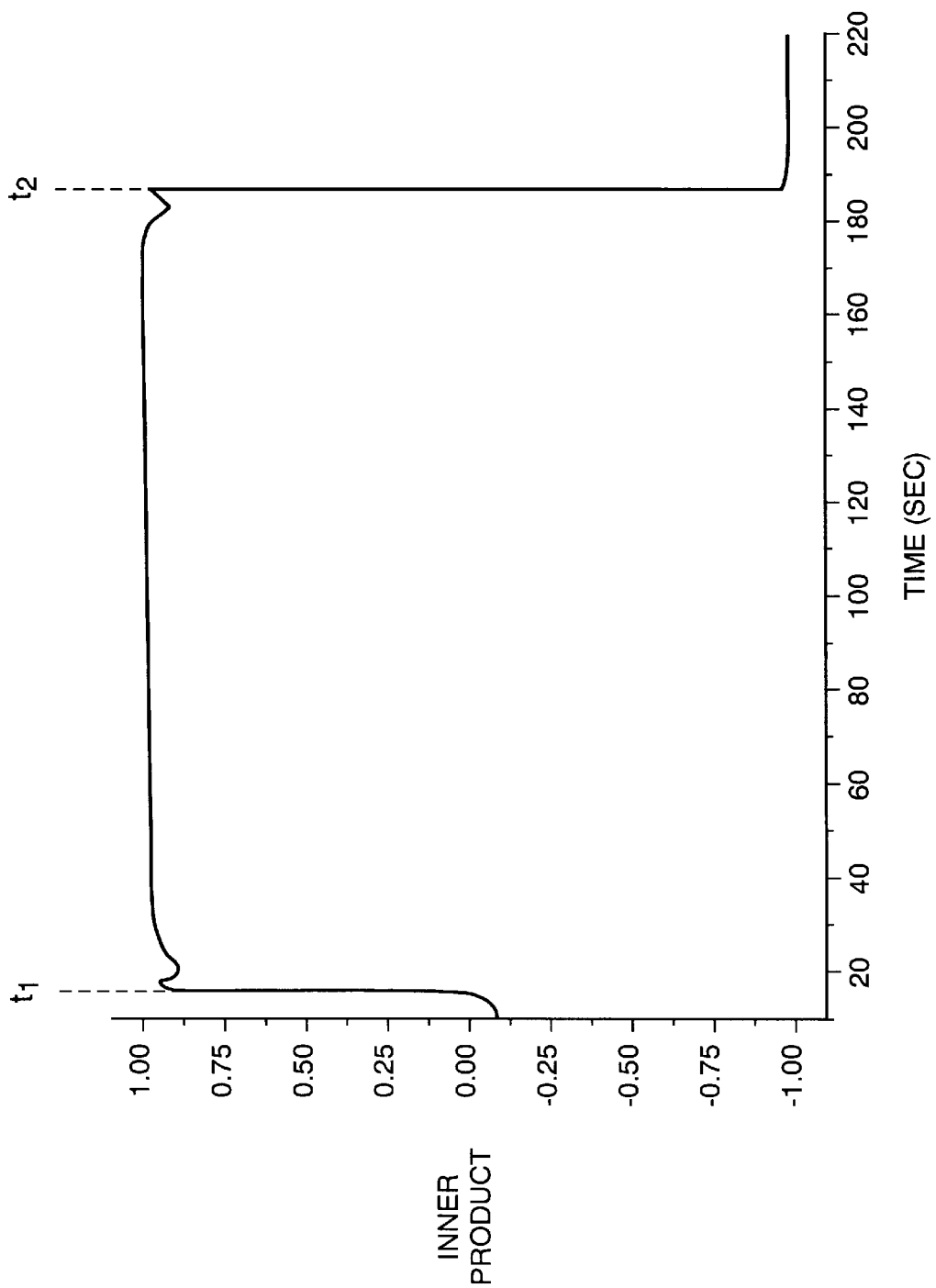
FIGS. 4A and 4B are graphs of the inner product of a calibration and a production principal component obtained during etching of the silicon dioxide layer of FIG. 3B without and with, respectively, a magnetic field applied during etching.

FIG. 4A is a graph of the inner product of the calibration principal component (e.g., PC1) of FIG. 3D with a production (first) principal component computed during a subsequent etch of the silicon dioxide layer 302 of FIG. 3B (employing the same processing conditions used to generate the OES data 300 of FIG. 3A). No magnetic field was applied. An evolving window comprising the five most recently obtained wavelength snap-shots (from the plasma 218) was employed to generate a new production principal component (e.g., a production PC1) every second. Each new production principal component was then compared to the calibration principal component of FIG. 3D by taking an inner product of the two principal components. It will be understood that other window sizes and other snap-shot rates may be employed.

With reference to FIG. 4A, at time to the plasma 218 is ignited and etching of the silicon dioxide layer 302 begins at time $t_1$. Etching continues until time $t_2$. Thereafter, at time $t_2$, the inner product of the calibration and production principal components changes sign from +1.0 to −1.0. This rapid change in the inner product identifies the endpoint for the etching of the oxide layer 302 with a degree of clarity unobservable with conventional endpoint detection techniques. The presence of endpoint at time $t_2$ was verified by other endpoint detection techniques.

Figure 4B:
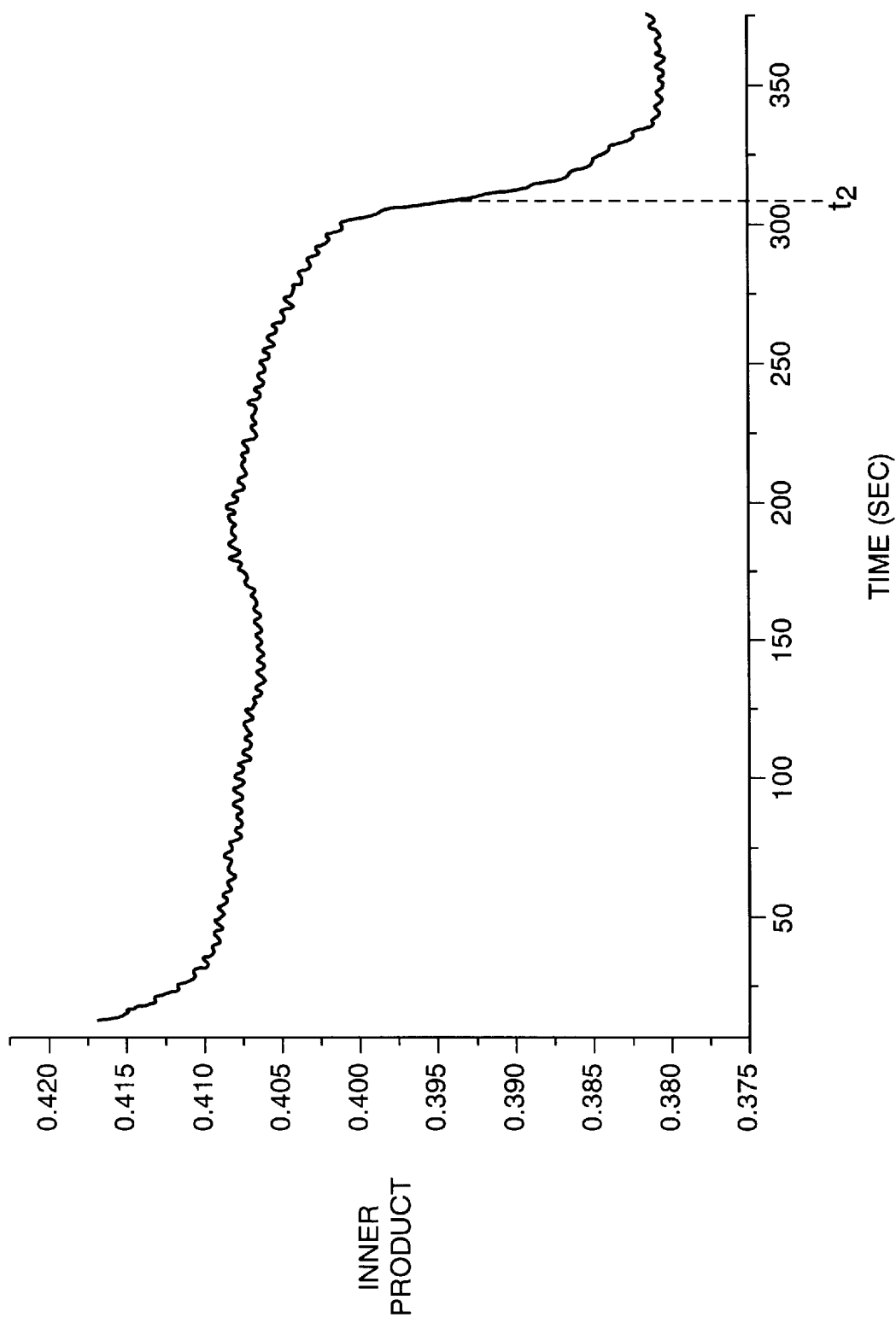

FIG. 4B is a graph of the inner product of the calibration principal component of FIG. 3D (computed with no magnetic field present during etching) with a production principal component computed during a subsequent etch of the silicon dioxide layer 302 of FIG. 3B employing the same processing conditions used to generate the OES data 300 of FIG. 3A, but with a 0.25 Hz magnetic field applied within the chamber. As can be seen in FIG. 4B, even though the calibration principal component was derived from a process having no magnetic field applied, a sharp transition still exists at time $t_2$ indicative of the etching endpoint for the silicon dioxide layer 302.

Figure 5A:
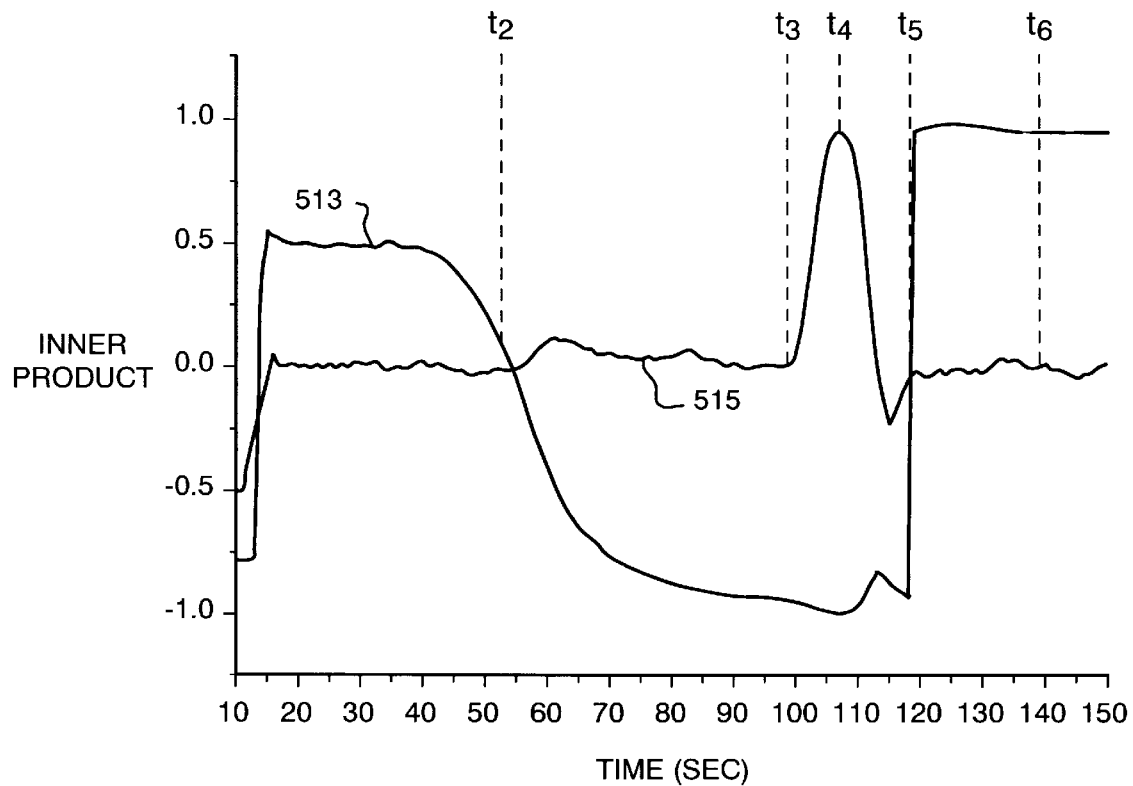
FIG. 5A is a graph of the inner product of calibration and production first principal components and calibration and production second principal components generated during the etching of a platinum multilayer structure.
Figure 5B:
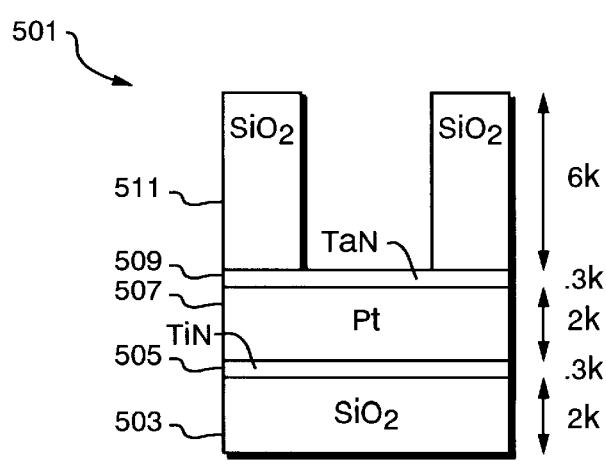
FIG. 5B is a cross-sectional diagram of a platinum multilayer structure that was etched to obtain the graph of FIG. 5A.

FIG. 5A is a graph of the inner product of a first principal component for a calibration process (calibration PC1) with a first principal component for a production process (production PC1) and of the inner product of a second principal component for a calibration process (calibration PC2) with a second principal component for a production process (production PC2) generated during the etching of a platinum multilayer structure 501 (FIG. 5B). The platinum multilayer structure 501 was etched using a chlorine-based etch chemistry, although any other known etch chemistry may be similarly employed.

The platinum multilayer structure 501 comprises a first silicon dioxide layer 503 deposited on a silicon wafer (not shown) and having a thickness of about 2000 angstroms, a titanium nitride layer 505 deposited on the first silicon dioxide layer 503 and having a thickness of about 300 angstroms, a platinum layer 507 deposited on the titanium nitride layer 505 and having a thickness of about 2000 angstroms, a tantalum nitride layer 509 deposited on the platinum layer 507 and having a thickness of about 300 angstroms and a second silicon dioxide layer 511 deposited on the tantalum nitride layer 509 and having a thickness of about 6000 angstroms. A portion of the second silicon dioxide layer 511 is removed to expose about 60% of the tantalum nitride layer 509 as shown. Because only about ⅛ of the silicon wafer (not shown) includes multilayer structures such as the multilayer structure 501, the net open area to be etched is approximately 7% of the total wafer area.

The small open area (e.g., about 7%) to be etched is particularly problematic for detecting the etching end point of the platinum layer 507. Platinum lines overlap intense molecular bands associated with the etch process and limit the use of single line intensity measurements. However, the inventive monitoring technique 100 of FIGS. 1A and 1B can easily identify the etching endpoint of the platinum layer 507.

To generate a suitable calibration principal component for detecting endpoint for the platinum layer 507 (as well as for titanium nitride layer 505 and for tantalum nitride layer 509), a series of reference etch processes were performed on the platinum multilayer structure 501 for varying time periods and the platinum multilayer structure 501 was examined following each etch process via scanning electron microscopy to identify the endpoint time for each layer 505–509 (times $t_6$, $t_5$ and $t_2$, respectively, in FIG. 5A). The scanning electron microscopy studies revealed that breakthrough of the tantalum nitride layer 509 and etching of the platinum layer 507 first occur at time $t_2$, that exposure of the titanium nitride layer 505 within the open area of the multilayer structure 501 begins at time $t_3$, that clearing of the platinum layer 507 in dense areas begins at time $t_4$ and that complete clearing of the platinum layer 507 occurs at time $t_5$. Further the titanium nitride layer 505 is cleared and the first silicon dioxide layer 503 is exposed at time $t_6$. Thereafter, to specifically target detection of endpoint for the platinum layer 507, the calibration PC1 and PC2 were computed near time $t_5$ as previously described (e.g., based on plasma emission wavelengths measured near time $t_5$). A subsequent "production" etch of the platinum multilayer structure 501 was performed under identical conditions to the reference etch process, and an evolving window was employed to generate a new production PC1 and a new production PC2 every second.

Each new production PC1 and PC2 was compared to the calibration PC1 and PC2, respectively, by taking an inner product of the first principal components and of the second principal components so as to generate a PC1 inner product curve 513 and a PC2 inner product curve 515, respectively. As shown in FIG. 5A, the etching endpoint for the platinum layer 507 is clearly identified at time $t_5$ by the PC1 inner product curve 513. Further, other etching features of the multilayer structure 501 such as plasma ignition at time $t_1$ and clearing/breakthrough of the tantalum nitride layer 509 at time $t_2$ are also identifiable. Note that to more accurately identify the etching endpoint of the titanium nitride layer 505 or of the tantalum nitride layer 509, calibration principal components may be generated near times $t_2$ and $t_6$ and employed within the inventive monitoring technique 100.

Figure 6A:
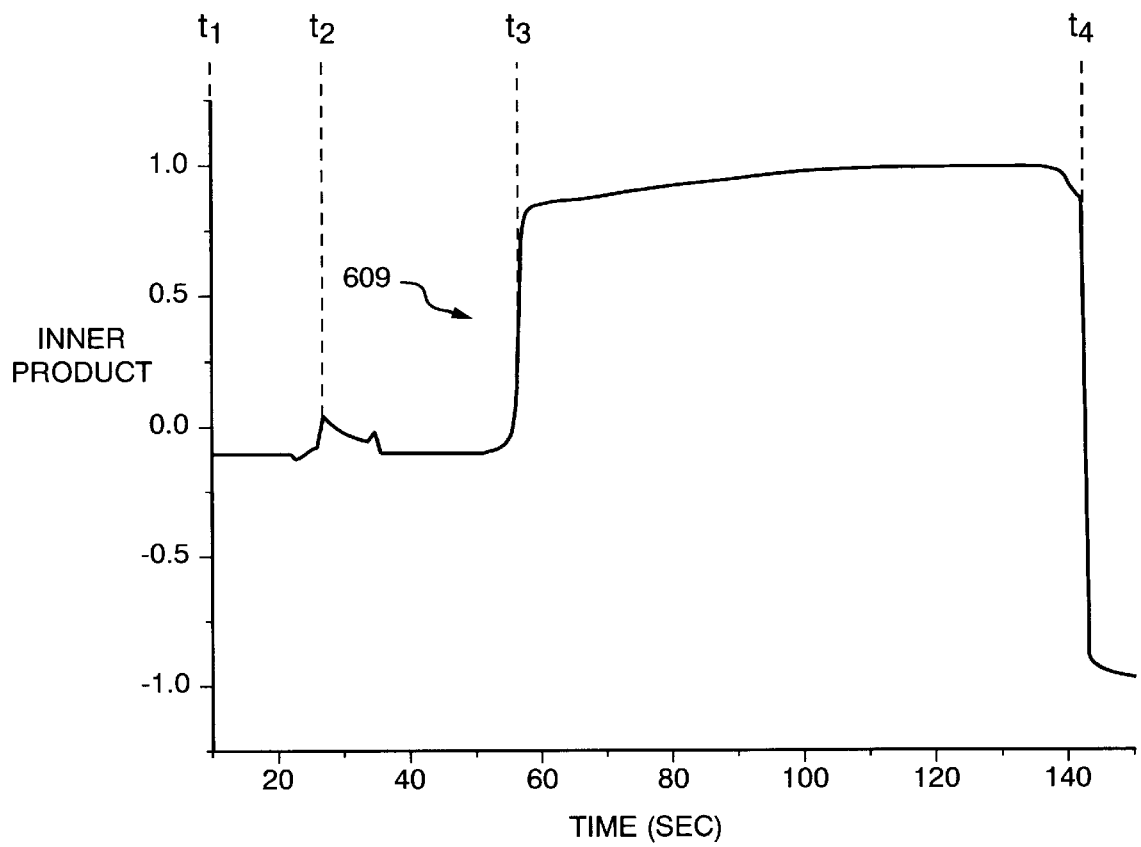
FIG. 6A is a graph of the inner product of calibration and production first principal components generated during the etching of a polysilicon multilayer structure.
Figure 6B:
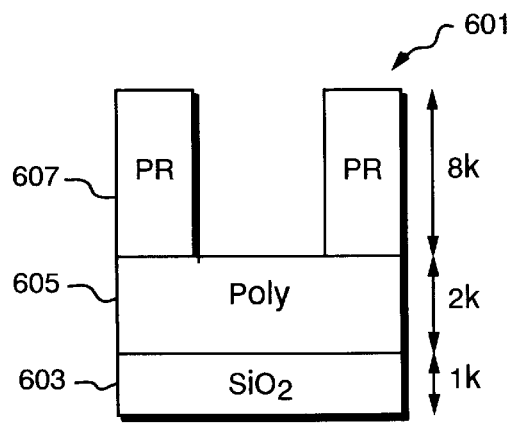
FIG. 6B is a cross-sectional diagram of a polysilicon multilayer structure that was etched to obtain the graph of FIG. 6A.

FIG. 6A is a graph of the inner product of a calibration PC1 with a production PC1 generated during the etching of a polysilicon multilayer structure 601 (FIG. 6B). The polysilicon multilayer structure 601 was etched using a bromine-chlorine based etch chemistry, although any other known etch chemistry may be similarly employed.

The polysilicon multilayer structure 601 comprises a silicon dioxide layer 603 deposited on a silicon wafer (not shown) and having a thickness of about 1000 angstroms, a polysilicon layer 605 deposited on the silicon dioxide layer 603 and having a thickness of about 2000 angstroms and a photoresist layer 607 deposited on the polysilicon layer 605 and having a thickness of about 8000 angstroms. The photoresist layer 607 is patterned to expose about 25% of the polysilicon layer 605. Based on prior etching experiments and/or knowledge of the inventors, it was suspected that during etching of the polysilicon multilayer structure 601, plasma stabilization would occur near time $t_1$, that $CF_4$ breakthrough would occur near time $t_2$, that etching of the polysilicon layer 605 would begin near time $t_3$, and continue to near time $t_4$, and that endpoint for the polysilicon layer 605 would occur near time $t_4$.

To confirm inventor suspicions, the inventive monitoring technique 100 was employed. A calibration PC1 was computed near time $t_4$ (e.g., based on plasma emission wavelengths measured near time $t_4$) and a subsequent, production etch of the polysilicon multilayer structure 601 was performed under conditions identical to the calibration etch process. An evolving window was employed to generate a new production PC1 every second, and the calibration and each new production PC1 were compared by taking an inner product of the principal components so as to generate the PC1 inner product curve 609 of FIG. 6A. As shown in FIG. 6A, the etching endpoint for the polysilicon layer 605 is clearly identified at time $t_4$ by the PC1 inner product curve 609. Further, other etching features of the multilayer structure 601 appear identifiable (e.g., plasma stabilization at time $t_1$, $CF_4$ breakthrough at time $t_2$, etc.)

Figure 7A:
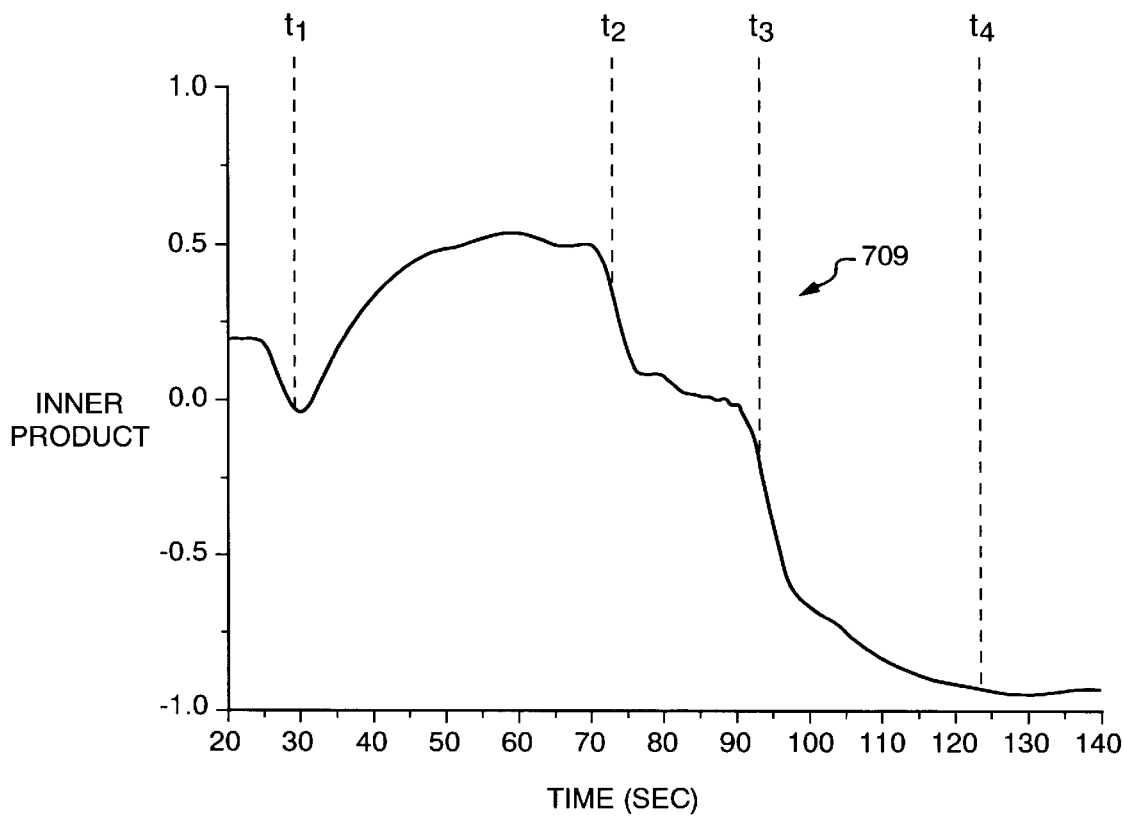
FIG. 7A is a graph of the inner product of calibration and production first principal components generated during the etching of a BARC multilayer structure.
Figure 7B:
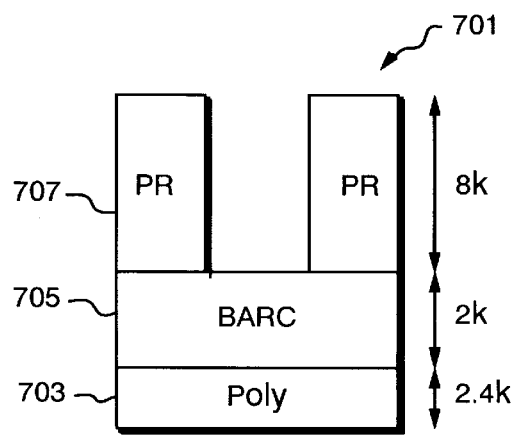
FIG. 7B is a cross-sectional diagram of a BARC multilayer structure that was etched to obtain the graph of FIG. 7A.

FIG. 7A is a graph of the inner product of a calibration PC1 with a production PC1 generated during the etching of a bottom-anti-reflective-coating (BARC) multilayer structure 701 (FIG. 7B). The multilayer structure 701 was etched using a bromine etch chemistry, although any other known etch chemistry may be similarly employed.

The BARC multilayer structure 701 comprises a polysilicon layer 703 deposited on a silicon wafer (not shown) and having a thickness of about 2400 angstroms, a BARC layer 705 deposited on the polysilicon layer 703 and having a thickness of about 2000 angstroms, and a photoresist layer 707 deposited on the BARC layer 705 and having a thickness of about 8000 angstroms. The photoresist layer 707 is patterned to expose about 2% of the BARC layer 705.

Because of the very small open area (e.g., 2%) of the BARC multilayer structure 701, and because photoresist and BARC have a similar material composition, no conventional endpoint techniques can clearly identify the etching endpoint of the BARC layer 705. However, the inventive monitoring technique 100 can identify the etching endpoint of the BARC layer 705.

As with the polysilicon multilayer structure 601 of FIG. 6B, based on prior etching experiments and/or knowledge of the inventors, it was suspected that during etching of the BARC multilayer structure 701, plasma ignition would occur near time $t_1$, the rim BARC would start to clear near time $t_2$, the die BARC would start to clear near time $t_3$ and the polysilicon layer 703 would be exposed near time $t_4$ (e.g., the PARC layer 705 would be cleared near time $t_4$).

To confirm inventor suspicions, the inventive monitoring technique 100 was employed. A calibration PC1 was computed near time $t_3$ (e.g., based on plasma emission wavelengths measured near time $t_3$) and a subsequent production etch of the multilayer structure 701 was performed under conditions identical to the calibration etch process. An evolving window was employed to generate a new production PC1 every second, and the calibration PC1 and each new production PC1 were compared by taking an inner product of the principal components so as to generate the PC1 inner product curve 709 of FIG. 7A. As shown in FIG.

7A, the etching endpoint for the BARC layer 705 is clearly identified near time by the PC1 inner product curve 709. Further, each etching feature of the multilayer structure 701 also appears identifiable (e.g., plasma ignition at time $t_1$, clearing of rim BARC at time $t_2$, and etching of the polysilicon layer 703 at time $t_4$).

While the inventive monitoring technique 100 primarily has been discussed in terms of endpoint detection with reference to FIGS. 3A–7A, it will be understood that other processing events such as plasma ignition, breakthrough, clearing and the like may be similarly identified. Further, the inventive monitoring technique 100 also can provide information about process state (e.g., RF power, plasma reaction chemistry, etc.) and about a process chamber (e.g., whether a fault exists, whether one chamber matches another chamber, etc.) by providing a "fingerprint" of the plasma process.

With regard to process state information, the shape and the position of the various features within the calibration and/or production principal components provide information that may be studied by varying processing parameters or conditions and by examining how the shape and the position of the features within the principal components change. For example, FIG. 8 is a graph of the inner product of a calibration PC1 with a production PC1 under conditions that mimic process drift. A calibration PC1 was generated by flowing 10 sccms of $C_4F_8$ during a plasma process within an inductively coupled plasma source (IPS) chamber. Thereafter, a production process was performed under identical process conditions with the exception that the flow rate of $C_4F_8$ was increased by 2 sccm every 60 seconds. As shown in FIG. 8, the changes in flow rate are easily discernible with the inventive monitoring technique 100 (e.g., at 60 seconds, 120 seconds, 180 seconds, etc.).

With regard to chamber information, one or more calibration principal component fingerprints of a plasma process taken when the plasma chamber 206 is known to be operating properly may serve as a "calibration" fingerprint for the process chamber. Thereafter, the principal component fingerprints of subsequent process runs may be periodically compared to the calibration fingerprint for the process. Drift, feature broadening, noise level or other similar changes in the subsequent principal component fingerprints can be quantified to serve as indicators of the health of the plasma chamber 206, and can identify chamber faults (e.g., via unique features attributable to each chamber fault). For example, following a chamber cleaning/maintenance operation, one or more production principal component fingerprints may be measured and compared to a calibration principal component calibration fingerprint for the chamber to ensure that the chamber is functioning properly following the cleaning/maintenance operation (e.g., as a "chamber qualification" process). The calibration and/or production principal component fingerprints of two different chambers also may be compared for chamber matching purposes, or to allow one chamber to be adjusted or "equalized" so as to match the principal component fingerprint of another chamber. Any number of production principal components and any principal components (e.g., PC1, PC2, PC3, etc.) for a process may be combined to serve as a calibration fingerprint for the process, if desired.

The inventive monitoring technique 100 may be performed manually (e.g., by the user 232) or automatically (e.g., by the processor 222) on a run-by-run basis or on a lot-by-lot basis if desired. Preferably computation of production principal components is performed as data is collected during a production process to allow processing parameters to be adjusted during processing (e.g., in real-time). With reference to FIG. 2, the user 232, a remote computer system for running a fabrication process, a manufacturing execution system, etc., may specify which process events (e.g., breakthrough, endpoint, etc.) the processor 222 should identify, and whether a warning should be sent to the plasma etching system 202 via the second control bus 230 in response thereto (e.g., to halt the plasma process within the plasma chamber 206), what process state information is desired (e.g., RF power, plasma reaction chemistry, etc.), whether real-time process control should be employed, what chamber information is desired (e.g., chamber fault information, chamber matching information, etc.) and whether the plasma process within the plasma chamber 206 should be halted if a chamber fault is detected. As stated, only a few plasma emissions wavelengths may be monitored, if desired.

Figure 9:
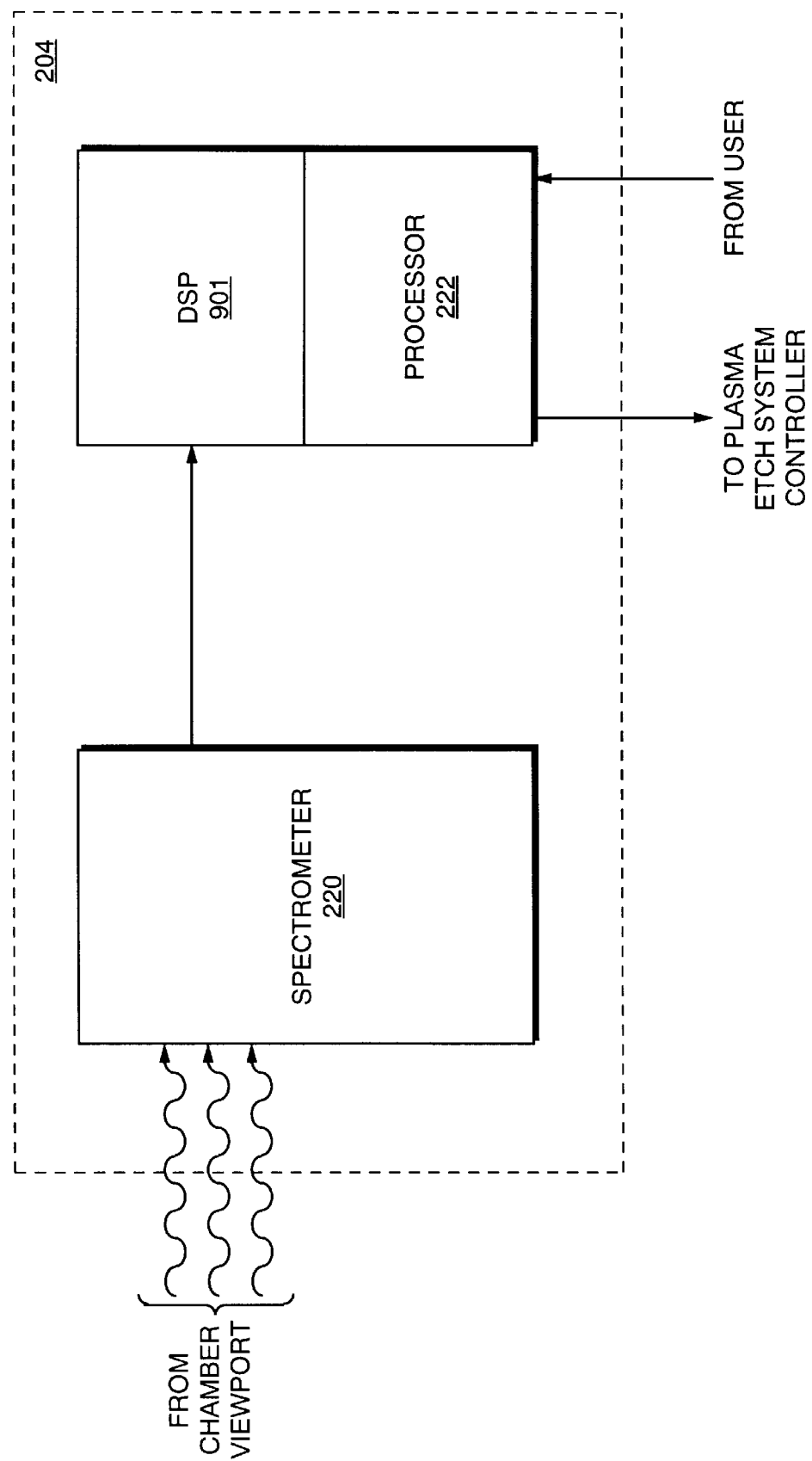
FIG. 9 is a schematic diagram of the inventive process monitoring system of FIG. 2 wherein a dedicated digital signal processor is employed.

FIG. 9 is a schematic diagram of the inventive process monitoring system 204 of FIG. 2 wherein a dedicated digital signal processor (DSP) 901 is employed. The DSP 901 preferably is programmed to define the evolving window for production principal component computations and to perform principal component analysis on the data within the evolving window (described previously) at a significantly higher rate than the processor 222. The DSP 901 then supplies the result principal component information to the processor 222 for analysis (e.g., for comparison with a calibration principal component). In this manner, analysis of OES data may be performed rapidly enough to allow for real-time processing parameter adjustment, if desired. Comparison of production and calibration principal components also may be performed within the DSP 901.

Figure 10:
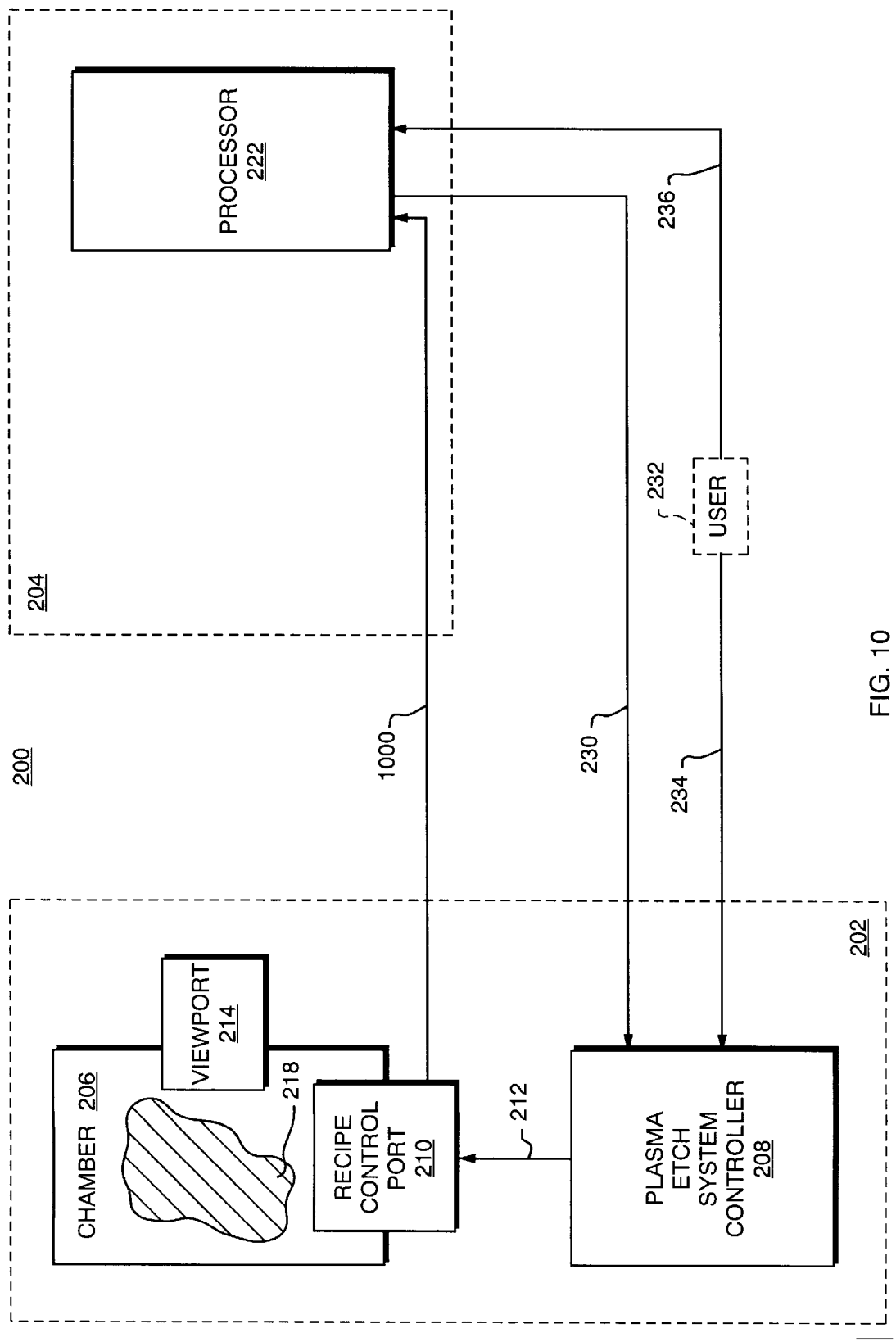
FIG. 10 is a schematic diagram of the inventive processing system of FIG. 2 wherein the process monitoring system is adapted to monitor RF power, wafer temperature, chamber pressure and throttle valve position.

In addition to monitoring plasma emission wavelengths as correlated attributes of a process, other (or additional) correlated attributes of a plasma process such as the RF power delivered to a wafer pedestal of a plasma chamber during plasma processing, wafer temperature, chamber pressure, throttle valve position, etc., may be monitored in accordance with the inventive monitoring technique 100 to obtain process state, process event and chamber information. FIG. 10 is a schematic diagram of the processing system 200 wherein the inventive process monitoring system 204 is adapted to monitor RF power, wafer temperature, chamber pressure, and throttle valve position during plasma processing rather than (or in addition to) plasma emission fluctuations. Specifically, within the inventive process monitoring system 204, the spectrometer 220 is no longer shown, and signals representative of the RF power, wafer temperature, chamber pressure and throttle valve position associated with the plasma chamber 206 during plasma processing are supplied to the processor 222 via a fifth control bus 1000 coupled between the recipe control port 210 and the processor 222. If the plasma etch system controller 208 directly interfaces the various mass flow controllers, RF generators, temperature controllers, pressure gauges, etc., of the plasma chamber 206 (e.g., without the recipe control port 210), correlated attribute information may be supplied to the processor 222 directly from the plasma etch controller 208. It will be understood that the spectrometer 220 may be employed to supply OES data to the processor 222 along with the other correlated attributes from the recipe control port 210 or from the plasma etch controller 208 (e.g., RF power, wafer temperature, etc.) if desired.

In general, signals delivered between any components within the processing system 200, whether or not delivered over a control bus, may be delivered in analog or digital form. For example, analog signals may be digitized via an analog-to-digital converter and transmitted via an RS-232 interface, a parallel interface, etc., if desired.

As with the plasma emission wavelengths, the processor 222 preferably uses an evolving window to generate a new production principal component, preferably at a period/c rate (e.g., every second), during the performance of a production process based on the RF power, wafer temperature, chamber pressure and throttle valve position information. The processor 222 then compares each new production principal component to a previously generated calibration principal component (as described) so as to obtain process event, process state and chamber information. The DSP 901 of FIG. 9 may be employed with the processor 222 to reduce analysis time.

Figure 11:
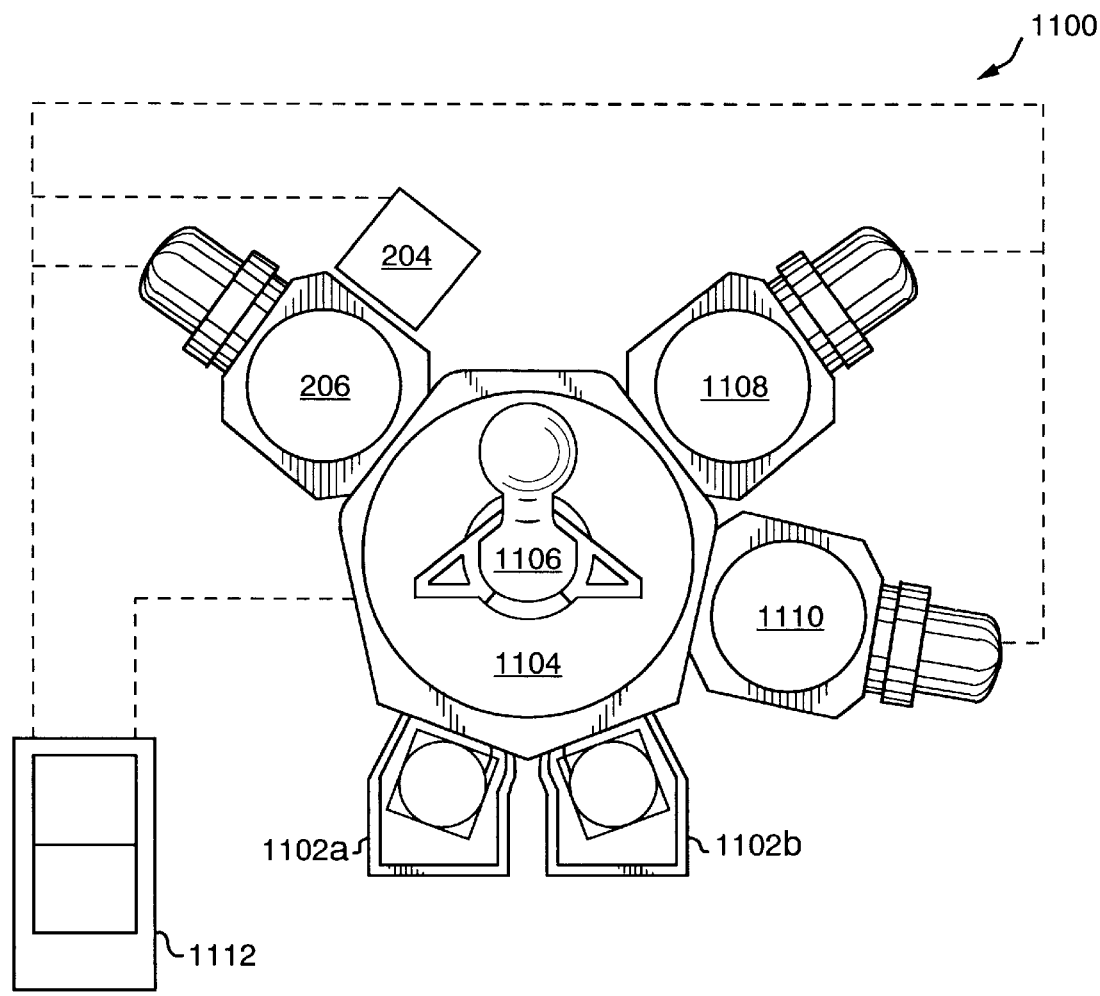
FIG. 11 is a top plan view of an automated tool for fabricating semiconductor devices that employs the inventive processing system of FIGS. 2 or 10.

FIG. 11 is a top plan view of an automated tool 1100 for fabricating semiconductor devices. The tool 1100 comprises a pair of load locks 1102a, 1102b, and a wafer handler chamber 1104 containing a wafer handler 1106. The wafer handler chamber 1104 and the wafer handler 1106 are coupled to a plurality of processing chambers 1108, 1110. Most importantly, the wafer handler chamber 1104 and the wafer handler 1106 are coupled to the plasma chamber 206 of the processing system 200 of FIG. 2 or 10. The plasma chamber 206 has the inventive process monitoring system 204 coupled thereto (as shown). The entire tool 1100 is controlled by a controller 1112 (e.g., a dedicated controller for the tool 1100, a remote computer system for running a fabrication process, a manufacturing execution system, etc.) having a program therein which controls semiconductor substrate transfer among the load locks 1102a, 1102b and the chambers 1108, 1110 and 206, and which controls processing therein.

The controller 1112 contains a program for controlling the process state of the plasma chamber 206 in real-time and for monitoring processing events (e.g., breakthrough, endpoint, etc.) in real-time via the inventive process monitoring system 204 as previously described with reference to FIGS. 1A–10. The inventive process monitoring system 204 allows for better control of the process state of the plasma chamber 206 and more accurately identifies when processing events occur therein (effectively increasing the throughput of the plasma chamber 206). Accordingly, both the yield and the throughput of the automated fabrication tool 1100 increases significantly.

In general, the process of measuring correlated attributes for a process (e.g., plasma electromagnetic emissions, RF power, chamber pressure, wafer temperature, throttle valve position, etc.), and the subsequent principal component analysis thereof may be performed by a user, by a remote computer system for running a fabrication process, by a manufacturing execution system, etc. As stated, analysis and monitoring preferably are performed during processing to allow for real-time process control. Preferably a user, a remote computer system for running a fabrication process, a manufacturing execution system or any other suitable controller, specifies which process events (e.g., breakthrough, endpoint, etc.) the processor 222 should identify, and whether a warning should be sent to the plasma etching system 202 in response thereto (e.g., to halt the plasma process within the plasma chamber 206), what process state information is desired (e.g., RF power, plasma reaction chemistry, etc.), whether real-time process control should be employed, what chamber information is desired (e.g., chamber fault information, chamber matching information, etc.) and whether the plasma process within the plasma chamber 206 should be halted if a chamber fault is detected. For example, a library of user selectable functions may be provided that direct the processor 222 to obtain desired process state, process event and/or chamber information and to act thereupon accordingly (e.g., to detect the endpoint of an etch process and to halt processing thereafter).

To identify processing events such as breakthrough and endpoint, and to obtain process chamber information such as chamber fault information and chamber matching information, a database comprising relevant process event or process chamber identification information (e.g., calibration principal components that provide endpoint information, breakthrough information, chamber matching information, etc.) may be provided within the processor 222, within a remote computer system for controlling a fabrication process, within a manufacturing execution system, etc. The relevant information within the database then is accessed by the processor 222 and is used to identify process events or to extract chamber information. For example, to detect endpoint or breakthrough during the etching of a material layer, one or more calibration principal components generated in the vicinity of the breakthrough or endpoint event may be stored within the database. Thereafter, during processing, production principal components may be compared to the one or more calibration principal components stored within the database. If the production and calibration principal components are within a predetermined range of each other, a signal may be generated to indicate that either endpoint or breakthrough has been detected. One or more calibration principal components indicative of endpoint or breakthrough for each material layer to be etched preferably are stored within the database.

With regard to process chamber information, one or more calibration principal component "fingerprints" of a process taken when the plasma chamber 206 is known to be operating properly may be stored within the database and serve as a "calibration" fingerprint for the process chamber. Thereafter, production principal component fingerprints computed during subsequent process runs may be periodically compared to the calibration fingerprint for the process stored within the database. Drift, feature broadening, noise level or other similar changes in the subsequent fingerprints can be quantified (e.g., via comparison with the calibration fingerprint) to serve as indicators of the health of the plasma chamber 206, and to identify chamber faults (e.g., via unique calibration or production principal component features attributable to each chamber fault that are stored within the database). For example, following a chamber cleaning/maintenance operation, a production principal component fingerprint may be measured and compared to a previously measured calibration principal component calibration fingerprint for the chamber to ensure that the chamber is functioning properly following the cleaning/maintenance operation. The calibration or production principal component fingerprints of two different chambers also may be compared for chamber matching purposes, or to allow one chamber to be adjusted or "equalized" so as to match the fingerprint of another chamber (as previously described). Principal component fingerprints also may be similarly employed to identify proper wafer chucking (e.g., as an improperly chucked wafer will generate unique principal component features during processing).

The foregoing description discloses only the preferred embodiments of the invention, modifications of the above disclosed apparatus and method which fall within the scope of the invention will be readily apparent to those of ordinary skill in the art. For instance, the monitored plasma emission wavelength ranges described herein merely are preferred, and other wavelength ranges may be monitored if desired. Production principal components need not be computed using an evolving window and/or may be computed only in the vicinity of an expected process event, plasma state or chamber state.

Further, while in FIGS. 2–11 the present invention has been described with reference to monitoring the process state of a semiconductor device fabrication process employing a plasma, it will be understood that in general, the present invention may be used to monitor any process having measurable correlated attributes (e.g., whether or not a plasma is employed and whether or not related to semiconductor device fabrication). For example, by monitoring correlated attributes such as temperature, pressure, weight (e.g., via a crystal microbalance), chemiluminescence, etc., of an arbitrary process in accordance with the present invention, process state information, process event information, and if applicable, chamber information may be obtained regarding the process. As another example, correlated attributes of deposition processes (e.g., chemical vapor deposition, plasma enhanced chemical vapor deposition and high density plasma chemical vapor deposition processes for the deposition of silicon nitride, tungsten silicide, polysilicon, low or high K materials, III–V or II–VI semiconductors, fluorinated silicon, triethylphosphate (TEPO) and tetraethyl orthosilicate (TEOS) films or any other materials) such as temperature, pressure, weight, plasma emissions, RF power, etc., may be monitored in accordance with the present invention to obtain process state, process event and chamber-related information. Such information may be used to monitor deposition rate, reaction chemistry, RF generator operation, etc., as well as for chamber fault and chamber matching purposes as previously described.

Accordingly, while the present invention has been disclosed in connection with the preferred embodiments thereof, it should be understood that other embodiments may fall within the spirit and scope of the invention, as defined by the following claims.

The invention claimed is:

1. A method of detecting an endpoint of a semiconductor fabrication process, comprising:

(a) performing a calibration process in which a first workpiece is exposed to a plasma;

(b) collecting first optical emission spectroscopy (OES) data for electromagnetic radiation emitted by the plasma during the calibration process;

(c) determining a timing of an endpoint that occurred during the calibration process;

(d) performing principal component analysis with respect to a window of the first OES data that corresponds to the determined endpoint timing to compute a principal component of the first OES data in the window.

(e) after steps (a)–(d), performing a production process in which a second workpiece is exposed to a plasma;

(f) collecting second OES data for electromagnetic radiation emitted by the plasma during the production process;

(g) for a series of windows of the second OES data, performing principal component analysis to compute a respective principal component for each window of the second OES data and comparing the principal component computed for each window with the principal component computed at step (d), wherein the comparing includes calculating inner products of the principal component computed at step (d) with the principal components computed at this step (g); and (h) detecting an endpoint of the production process based on a result of step (g).

2. The method of claim 1, wherein step (h) includes detecting a transition in the calculated inner products.

3. The method of claim 1, wherein the workpieces are silicon wafers each having a multilayer semiconductor structure.

4. The method of claim 3, wherein the calibration process and the production process each include etching a layer of a multilayer semiconductor structure.

5. The method of claim 4, wherein the etched layer includes silicon dioxide.

6. The method of claim 4, wherein the etched layer includes a metal.

7. The method of claim 4, wherein the etched layer includes polysilicon.

8. The method of claim 4, wherein the etched layer includes a bottom-anti-reflective-coating.

9. The method of claim 1, wherein the first and second OES data are collected for electromagnetic emissions having wavelengths from about 180 to 850 nanometers.

10. The method of claim 1, wherein the first and second OES data is mean-centered before performing the principal component analyses.

11. The method of claim 1, wherein step (c) includes microscopic examination of the workpiece.

12. The method of claim 1, wherein steps (f)–(h) are performed concurrently with step (e).

13. The method of claim 1, wherein the series of windows of the second OES data are generated at intervals of about one second.

14. The method of claim 1, wherein the endpoint detected at step (h) is completion of an etching process.

* * * * *